(12) United States Patent
Feng et al.

(10) Patent No.: US 7,977,330 B2
(45) Date of Patent: Jul. 12, 2011

(54) SALTS AND CRYSTAL MODIFICATIONS THEREOF

(75) Inventors: Lilli Feng, Pine Brook, NJ (US); Xinglong Jiang, Hillsborough, NJ (US); Piotr H. Karpinski, Lincoln Park, NJ (US)

(73) Assignee: Novartis AG, Basel (CH)

( * ) Notice: Subject to any disclaimer, the term of this patent is extended or adjusted under 35 U.S.C. 154(b) by 230 days.

(21) Appl. No.: 12/298,203

(22) PCT Filed: May 21, 2007

(86) PCT No.: PCT/US2007/069327
§ 371 (c)(1),
(2), (4) Date: Oct. 23, 2008

(87) PCT Pub. No.: WO2007/140154
PCT Pub. Date: Dec. 6, 2007

(65) Prior Publication Data
US 2009/0163478 A1    Jun. 25, 2009

Related U.S. Application Data

(60) Provisional application No. 60/802,836, filed on May 23, 2006.

(51) Int. Cl.
*C07D 243/24* (2006.01)
*A61K 31/5513* (2006.01)
*A61P 31/12* (2006.01)
(52) U.S. Cl. ........................................ 514/221; 540/509
(58) Field of Classification Search .................. 540/509; 514/221
See application file for complete search history.

(56) References Cited

FOREIGN PATENT DOCUMENTS
WO     2004026843    12/2007

OTHER PUBLICATIONS

Carter, Malcolm et al., "1,4-Benzodiazepines as Inhibitors of Respiratory Syncytial Virus.", Journal of Medicinal Chemistry, Apr. 6, 2006, vol. 49, No. 7, pp. 2311-2319.

*Primary Examiner* — Bruck Kifle
(74) *Attorney, Agent, or Firm* — McCarter & English, LLP; Elizabeth A. Hanley, Esq.; Jermaine A. Lawrence, Esq.

(57) ABSTRACT

The invention relates to salts of 1-(2-Fluoro-phenyl)-3-(2-oxo-5-phenyl-2,3-dihydro-1H-benzo[e][1,4]diazepin-3-yl)-urea and crystalline forms thereof, their production and usage, and pharmaceutical preparations containing such salts and crystalline forms.

15 Claims, 6 Drawing Sheets

SALTS AND CRYSTAL MODIFICATIONS THEREOF

The present invention relates to salts of 1-(2-Fluoro-phenyl)-3-(2-oxo-5-phenyl-2,3-dihydro-1H-benzo[e][1,4]diazepin-3-yl)-urea and crystalline forms thereof. Also provided are processes for the preparation thereof, pharmaceutical compositions comprising the compounds of the present invention and uses thereof in therapeutic treatment of warm-blooded animals, especially humans.

1-(2-Fluoro-phenyl)-3-(2-oxo-5-phenyl-2,3-dihydro-1H-benzo[e][1,4]diazepin-3-yl)-urea can be represented by the following formula

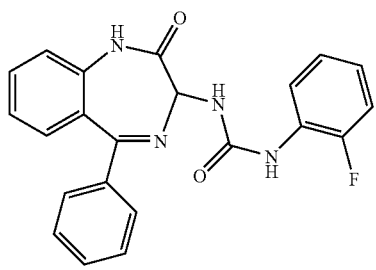

(I)

and is known from WO2004/026843, the entire disclosure of which is incorporated by reference, and can be synthesized as described therein. The present invention relates to novel and improved salts of the known compound of formula I. The compounds of the formula I include racemic or enantiomeric forms. Particularly preferred, in accordance with the present invention, is the S enantiomer of formula I as represented by formula Ia:

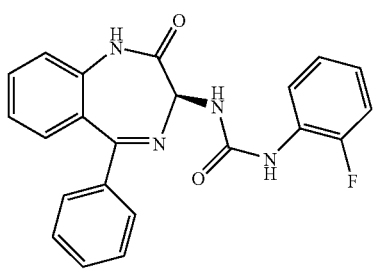

(Ia)

The free base of 1-(2-Fluoro-phenyl)-3-(2-oxo-5-phenyl-2,3-dihydro-1H-benzo[e][1,4]diazepin-3-yl)-urea shows low solubility in aqueous media, which makes it difficult to formulate 1-(2-Fluoro-phenyl)-3-(2-oxo-5-phenyl-2,3-dihydro-1H-benzo[e][1,4]diazepin-3-yl)-urea into pharmaceutical compositions, in particular for e.g. high-dose or intravenous (IV) formulations In accordance with the present invention it has now surprisingly been found that difficulties in formulating the free base can be overcome with the compounds of the present invention. It has been found that, unexpectedly, salts of the compound of formula I with benzene sulfonic acid possess particularly beneficial pharmacokinetic properties and have further been found to possess a unique combination of favorable formulation properties which make them particularly suitable for the preparation of pharmaceutical compositions of 1-(2-Fluoro-phenyl)-3-(2-oxo-5-phenyl-2,3-dihydro-1H-benzo[e][1,4]diazepin-3-yl)-urea adapted for systemic administration.

Furthermore, it has been surprisingly found in accordance with the present invention that under certain conditions crystalline forms can be obtained from the besylate salt of 1-(2-Fluoro-phenyl)-3-(2-oxo-5-phenyl-2,3-dihydro-1H-benzo[e][1,4]diazepin-3-yl)-urea. Such crystalline forms show improved stability and purity and thus e.g. easier handling in plant. The crystalline forms of 1-(2-Fluoro-phenyl)-3-(2-oxo-5-phenyl-2,3-dihydro-1H-benzo[e][1,4]diazepin-3-yl)-urea are preferably essentially pure. The term essentially pure in accordance with the present invention means that the sum of related substances is less than 1%, preferably less than 0.75%, more preferably less than 0.5% and that the residual solvents and water are less than 1%, preferably less than 0.75%, more preferably less than 0.5% and still more preferably less than 0.25% by weight.

In accordance with the present invention it has further surprisingly been found that crystalline 1-(2-Fluoro-phenyl)-3-(2-oxo-5-phenyl-2,3-dihydro-1H-benzo[e][1,4]diazepin-3-yl)-urea besylate can be recovered as a hydrate. Accordingly, in a preferred embodiment, the crystalline form 1-(2-Fluoro-phenyl)-3-(2-oxo-5-phenyl-2,3-dihydro-1H-benzo[e][1,4]diazepin-3-yl)-urea besylate is hydrated, particularly preferred is the monohydrate. In an other preferred embodiment the crystalline form of 1-(2-Fluoro-phenyl)-3-(2-oxo-5-phenyl-2,3-dihydro-1H-benzo[e][1,4]diazepin-3-yl)-urea besylate is not hydrated, i.e. the anhydrate. The anhydrate can e.g. be prepared by dehydration of the monohydrate under suitable conditions. The hydrate such as e.g. the monohydrate of the beslyate salt of compound I shows particularly good solubility properties in aqueous media thereby opening up new possibilities for improved formulation of pharmaceutical compositions for compounds of formula I, such as e.g. high dose formulations or IV formulation.

The polymorphic form of the besylate monohydrate salt of 1-(2-Fluoro-phenyl)-3-(2-oxo-5-phenyl-2,3-dihydro-1H-benzo[e][1,4]diazepin-3-yl)-urea according to the present invention typically dehydrates at about 115° C. (onset, broad peak) when analyzed by differential scanning calorimetry at a heating rate of 10° C./min. However, it is understood that melting points are dependent e.g on the conditions in which they are measured or e.g. on the purity of the sample and thus may vary. This corresponds to about 3.2% weight loss at about 130° C. when analyzed by thermogravimetric analysis at a heating rate of 10° C./min. The polymorphic form of the besylate anhydrate salt of 1-(2-Fluoro-phenyl)-3-(2-oxo-5-phenyl-2,3-dihydro-1H-benzo[e][1,4]diazepin-3-yl)-urea can be characterized by melting onset temperature of about 170 to 175° C., preferably about 173° C. Melting points are determined by means of a DSC thermogram using a TA DSC Q1000. DSC ("differential scanning calorimetry") Using this technique, the melting temperature of the polymorphic forms can be measured by heating the samples until a thermal, i.e. an endothermic reaction is detected by means of ultrasensitive sensors. The melting points indicated in this text are determined using a TA DSC Q1000 apparatus, about 1 to 3 mg of each sample being measured in an aluminium crucible with a—lid under an atmosphere of nitrogen at a heating rate of 10° C./min (starting at 30° C.).

FIG. 1 shows the X-ray diffraction diagram of the crystalline besylate monohydrate salt of 1-(2-Fluoro-phenyl)-3-(2-oxo-5-phenyl-2,3-dihydro-1H-benzo[e][1,4]diazepin-3-yl)-urea. In the X-ray diagram, the angle of diffraction 2theta is plotted on the horizontal axis (x-axis) and the peak intensity on the vertical (y-axis). X-ray powder diffraction patterns are measured on a Bruker D8 Discover diffractometer with Cu Kα radiation source (Kα1 radiation, wavelength λ=1.54056 Angström). Accordingly, there is provided a crystalline form of the besylate monohydrate salt of 1-(2-Fluoro-phenyl)-3-(2-oxo-5-phenyl-2,3-dihydro-1H-benzo[e][1,4]diazepin-3-yl)-urea wherein said crystalline form is characterized by at least one of the following diffraction peaks at angles of diffraction 2theta (±0.5°): 7.5, 9.5, 11.9, 12.1, 15.4, 16.3, 17.1, 19.0, 19.4, 20.6, 21.3, 22.1, 22.5, 23.1, 23.6, 24.2, 24.7, 25.8, 26.8, 27.8, 29.2, 29.7, 30.5, 32.0, 32.3, 36.4, 37.3. As appreciated by the person of skill in the art, the relative intensities of the diffractions can vary depending e.g. on the sample preparation or the instrument used and also, some of the above peaks may not always be detectable. Thus, in one embodiment, the present invention provides a crystalline form of the besylate monohydrate salt of 1-(2-Fluoro-phenyl)-3-(2-oxo-5-phenyl-2,3-dihydro-1H-benzo[e][1,4]diazepin-3-yl)-urea wherein said form has a X-ray powder diffraction pattern including a characteristic peak at an angle of diffraction 2theta of 7.5°. In another embodiment, the present invention provides a crystalline form of the besylate monohydrate salt of 1-(2-Fluoro-phenyl)-3-(2-oxo-5-phenyl-2,3-dihydro-1H-benzo[e][1,4]diazepin-3-yl)-urea which has a X-ray powder diffraction pattern including further characteristic peak(s) at an angle of diffraction 2theta of 21.3° and/or 23.1°.

FIG. 6 shows the X-ray diffraction diagram of the anhydrous crystalline besylate salt of 1-(2-Fluoro-phenyl)-3-(2-oxo-5-phenyl-2,3-dihydro-1H-benzo[e][1,4]diazepin-3-yl)-urea. Accordingly, there is provided a crystalline form of the anhydrous besylate salt of 1-(2-Fluoro-phenyl)-3-(2-oxo-5-phenyl-2,3-dihydro-1H-benzo[e][1,4]diazepin-3-yl)-urea wherein said crystalline form is characterized by at least one of the following diffraction peaks at angles of diffraction 2theta (±0.5°): 5.8, 10.3, 11.8, 12.0, 13.5, 14.5, 16.1, 16.7, 17.4, 18.2, 19.0, 19.7, 20.2, 20.6, 21.1, 21.6, 22.1, 22.7, 23.7, 24.8, 25.1, 25.7, 26.8, 28.3, 30.7, 33.2, 35.0, 35.5, 39.0, 39.2. As appreciated by the person of skill in the art, the relative intensities of the diffractions can vary depending e.g. on the sample preparation or the instrument used and also, some of the above peaks may not always be detectable. Thus, in one embodiment, the present invention provides a crystalline form of the anhydrous besylate salt of 1-(2-Fluoro-phenyl)-3-(2-oxo-5-phenyl-2,3-dihydro-1H-benzo[e][1,4]diazepin-3-yl)-urea wherein said form has a X-ray powder diffraction pattern including a characteristic peak at an angle of diffraction 2theta of 25.10. In another embodiment, the present invention provides a crystalline form of the besylate monohydrate salt of 1-(2-Fluoro-phenyl)-3-(2-oxo-5-phenyl-2,3-dihydro-1H-benzo[e][1,4]diazepin-3-yl)-urea which has a X-ray powder diffraction pattern further including one or several or all of the characteristic peak(s) at an angle of diffraction 2theta of 14.5°, 22.7°, 22.1°, 20.2° and/or 23.7°.

TABLE 1

List of most significant diffraction peaks of the crystalline besylate monohydrate salt of 1-(2-Fluoro-phenyl)-3-(2-oxo-5-phenyl-2,3-dihydro-1H-benzo[e][1,4]diazepin-3-yl)-urea.

| Position (2-theta) | d-spacing (Å) | Intensity count | Rel. Intensity % |
|---|---|---|---|
| 7.547 | 11.70362 | 92.1 | 100 |
| 9.537 | 9.26556 | 19.4 | 21.1 |
| 11.897 | 7.43296 | 9.72 | 10.6 |
| 12.12 | 7.2964 | 8.75 | 9.5 |
| 15.393 | 5.75148 | 9.5 | 10.3 |
| 16.304 | 5.4323 | 20.6 | 22.4 |
| 17.075 | 5.18855 | 29 | 31.5 |
| 19.048 | 4.65548 | 17.9 | 19.5 |
| 19.433 | 4.56407 | 15.5 | 16.8 |
| 20.628 | 4.30231 | 22.6 | 24.5 |
| 21.273 | 4.1733 | 76.7 | 83.3 |
| 22.077 | 4.02298 | 12.6 | 13.7 |
| 22.548 | 3.93994 | 18.5 | 20 |
| 23.077 | 3.85096 | 43.9 | 47.6 |
| 23.628 | 3.7623 | 22 | 23.9 |
| 24.154 | 3.68153 | 33.9 | 36.8 |
| 24.699 | 3.60152 | 31.7 | 34.4 |
| 25.773 | 3.45379 | 31.5 | 34.2 |
| 26.786 | 3.32548 | 14.6 | 15.9 |
| 27.802 | 3.20628 | 16.3 | 17.7 |
| 29.218 | 3.05394 | 15 | 16.3 |
| 29.696 | 3.00595 | 13.7 | 14.9 |
| 30.517 | 2.92685 | 21.4 | 23.2 |
| 31.969 | 2.79719 | 16.9 | 18.3 |
| 32.324 | 2.76723 | 23.1 | 25.1 |
| 36.371 | 2.4681 | 12.1 | 13.1 |
| 37.328 | 2.40699 | 12 | 13.1 |

TABLE 2

List of most significant diffraction peaks of the anhydrous crystalline besylate salt of 1-(2-Fluoro-phenyl)-3-(2-oxo-5-phenyl-2,3-dihydro-1H-benzo[e][1,4]diazepin-3-yl)-urea.

| Position (2-theta) | d-spacing (Å) | Intensity count | Rel. Intensity % |
|---|---|---|---|
| 5.827 | 15.15437 | 14.8 | 52.1 |
| 10.34 | 8.54834 | 9.96 | 34.9 |
| 11.768 | 7.51357 | 8.94 | 31.4 |
| 12.02 | 7.35688 | 8.1 | 28.4 |
| 13.492 | 6.55723 | 19.2 | 67.5 |
| 14.479 | 6.11268 | 25.9 | 90.9 |
| 16.106 | 5.49864 | 11.2 | 39.2 |
| 16.698 | 5.30487 | 12 | 42.3 |
| 17.407 | 5.0905 | 14.9 | 52.3 |
| 18.221 | 4.86466 | 15.2 | 53.2 |
| 18.96 | 4.67686 | 11.7 | 40.9 |
| 19.72 | 4.49821 | 14.6 | 51.3 |
| 20.228 | 4.38632 | 20.3 | 71.4 |
| 20.604 | 4.30716 | 15.7 | 55 |
| 21.088 | 4.20947 | 15.9 | 55.8 |
| 21.564 | 4.11755 | 17.4 | 61.1 |
| 22.13 | 4.01354 | 20.9 | 73.5 |
| 22.666 | 3.91978 | 22.1 | 77.5 |
| 23.67 | 3.7557 | 20.1 | 70.5 |
| 24.8 | 3.58711 | 17.6 | 61.7 |
| 25.136 | 3.53987 | 28.5 | 100 |
| 25.735 | 3.45885 | 14.9 | 52.3 |
| 26.799 | 3.32394 | 18.5 | 64.9 |
| 28.282 | 3.15292 | 14.5 | 50.9 |
| 30.668 | 2.9128 | 13.8 | 48.3 |
| 33.204 | 2.69594 | 11.9 | 41.8 |
| 34.999 | 2.56164 | 10.8 | 37.8 |
| 35.519 | 2.52533 | 10.6 | 37.3 |
| 39.035 | 2.30555 | 6.58 | 23.1 |
| 39.218 | 2.29521 | 5.7 | 20 |

In accordance with the present invention, the observed angle of diffraction 2theta can deviate ±0.1°, ±0.2°, ±0.3° or ±0.5°, or up to ±10% or ±20% of the above angles of refraction.

FIG. 2 shows the FT-IR spectrum of the crystalline 1-(2-Fluoro-phenyl)-3-(2-oxo-5-phenyl-2,3-dihydro-1H-benzo[e][1,4]diazepin-3-yl)-urea besylate monohydrate. The FT-IR spectrum was recorded using a Nicolet Magna-IR560. The sample was tested as is using ATR (attentenous total reflectance) sampling device. The crystalline form can be characterized by the following major IR bands: 1696 cm$^{-1}$, 1540 cm$^{-1}$, 1189 cm$^{-1}$, 1126 cm$^{-1}$, 1034 cm$^{-1}$. and 1016 cm$^{-1}$. More broadly by the following IR bands: 3289 cm$^{-1}$, 3080 cm$^{-1}$, 2892 cm$^{-1}$, 1696 cm$^{-1}$, 1606 cm$^{-1}$, 1540 cm$^{-1}$, 1493 cm$^{-1}$, 1478 cm$^{-1}$, 1458 cm$^{-1}$, 1444 cm$^{-1}$, 1379 cm$^{-1}$, 1351 cm$^{-1}$, 1328 cm$^{-1}$, 1309 cm$^{-1}$, 1261 cm$^{-1}$, 1222 cm$^{-1}$, 1189 cm$^{-1}$, 1126 cm$^{-1}$, 1107 cm$^{-1}$, 1071 cm$^{-1}$, 1034 cm$^{-1}$, 1016 cm$^{-1}$, 996 cm$^{-1}$, 962 cm$^{-1}$, 943 cm$^{-1}$, 932 cm$^{-1}$, 879 cm$^{-1}$, 834 cm$^{-1}$, 787 cm$^{-1}$, 764 cm$^{-1}$, 733 cm$^{-1}$, 697 cm$^{-1}$, 670 cm$^{-1}$, 645 cm$^{-1}$, 621 cm$^{-1}$, 604 cm$^{-1}$, 564 cm$^{-1}$ and 537 cm$^{-1}$.

Figure 1:
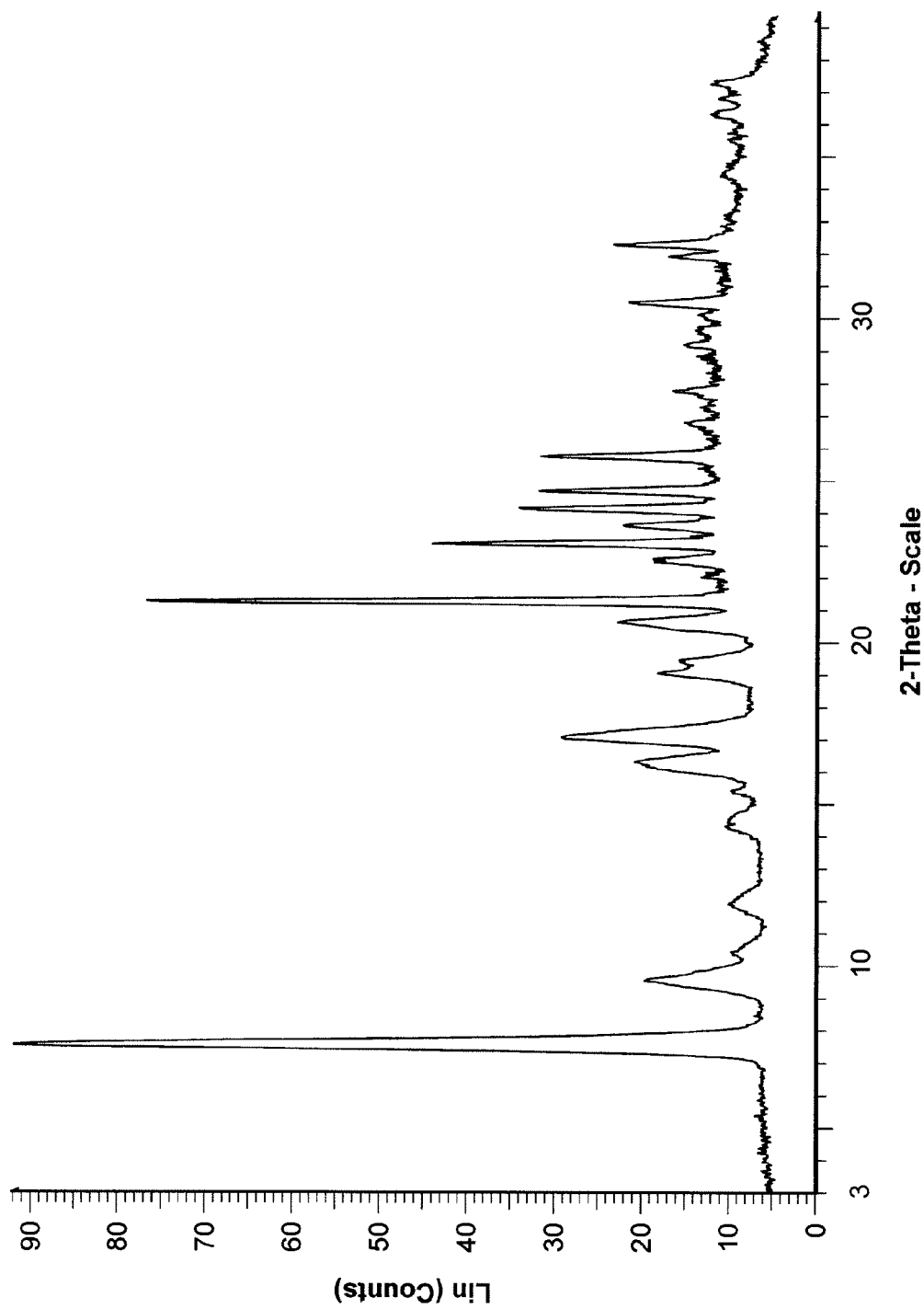
Figure 2:
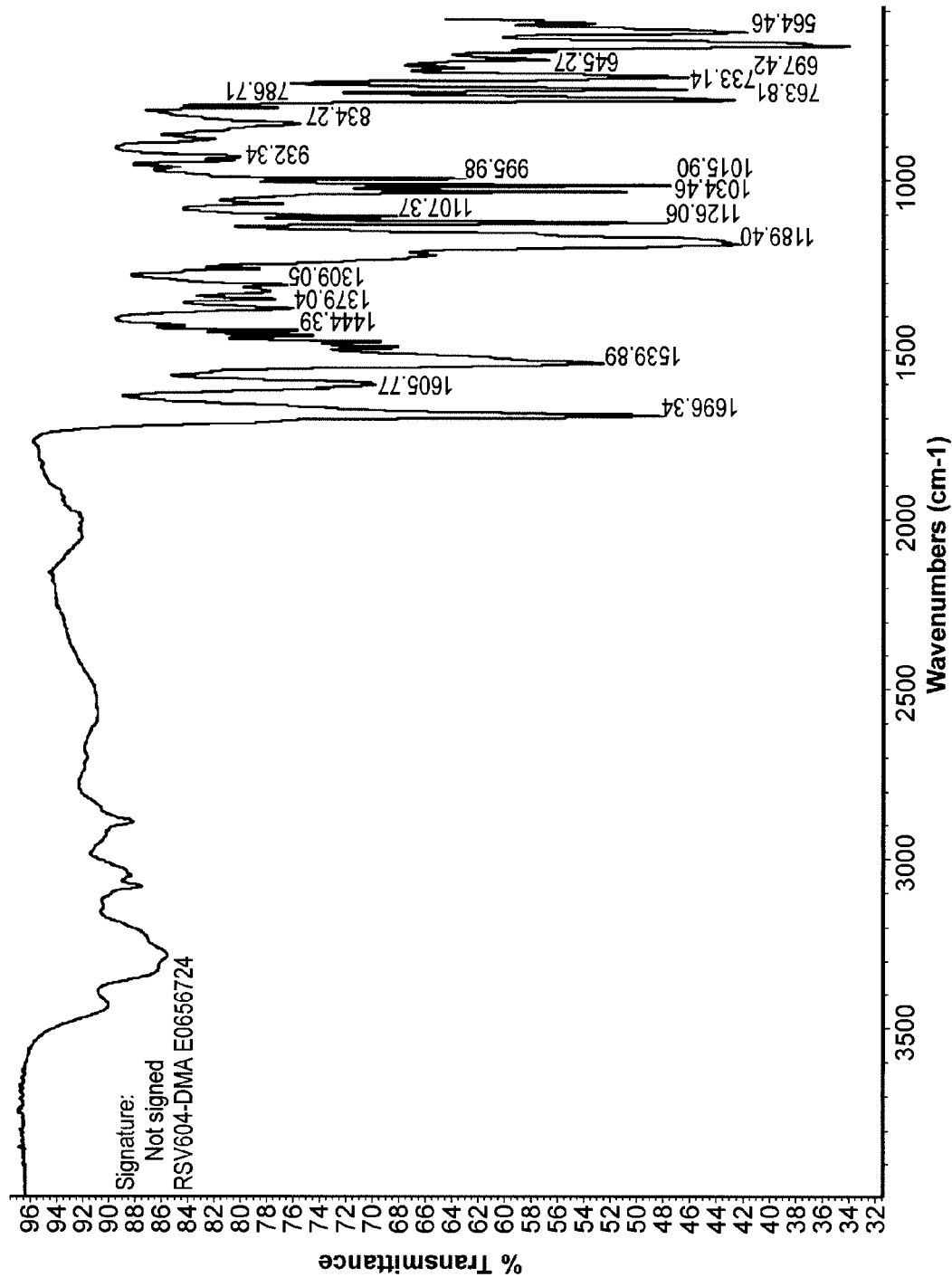
Figure 3:
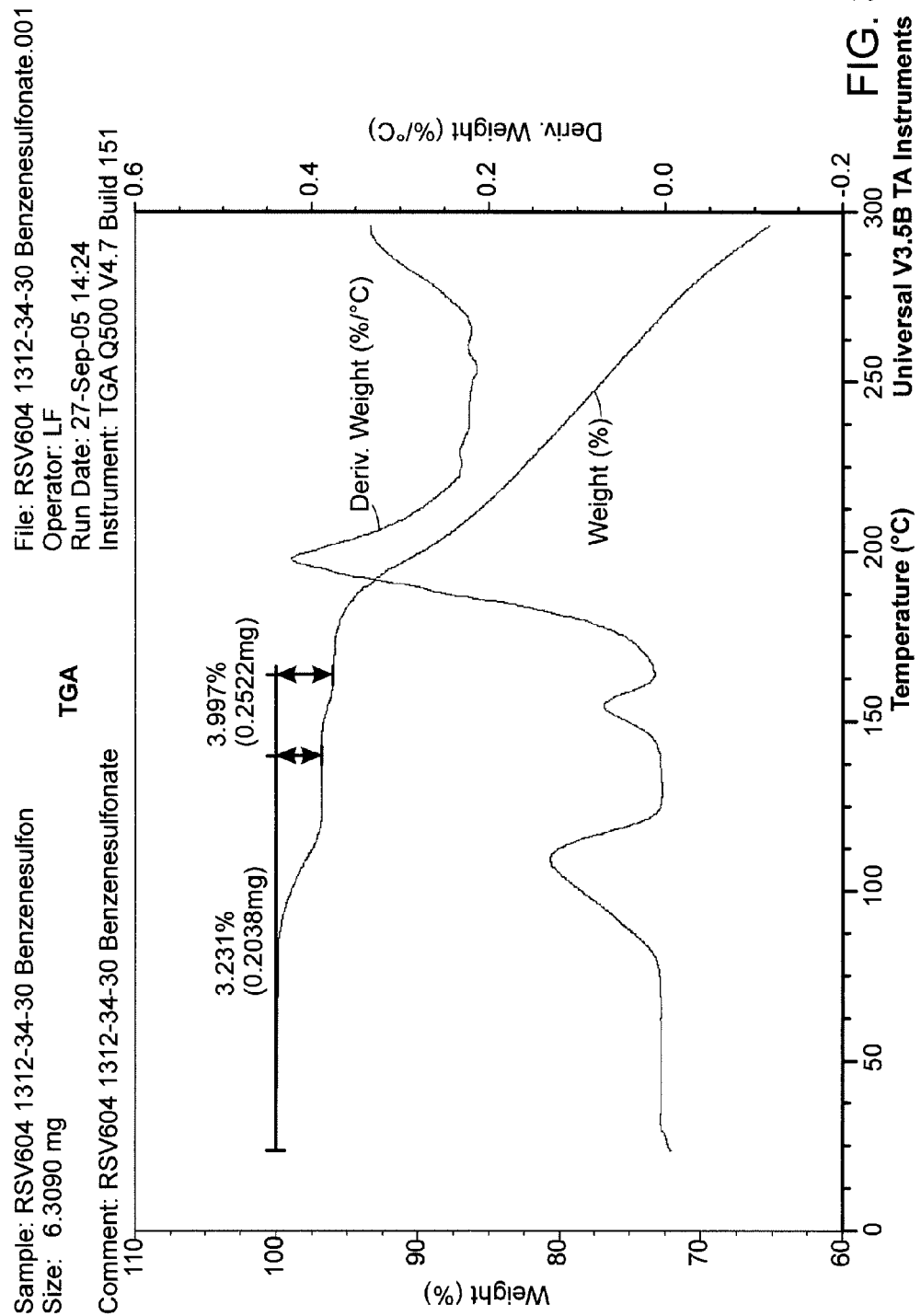
FIG. 3 shows the TGA curve of crystalline 1-(2-Fluoro-phenyl)-3-(2-oxo-5-phenyl-2,3-dihydro-1H-benzo[e][1,4]diazepin-3-yl)-urea besylate monohydrate.
Figure 4:
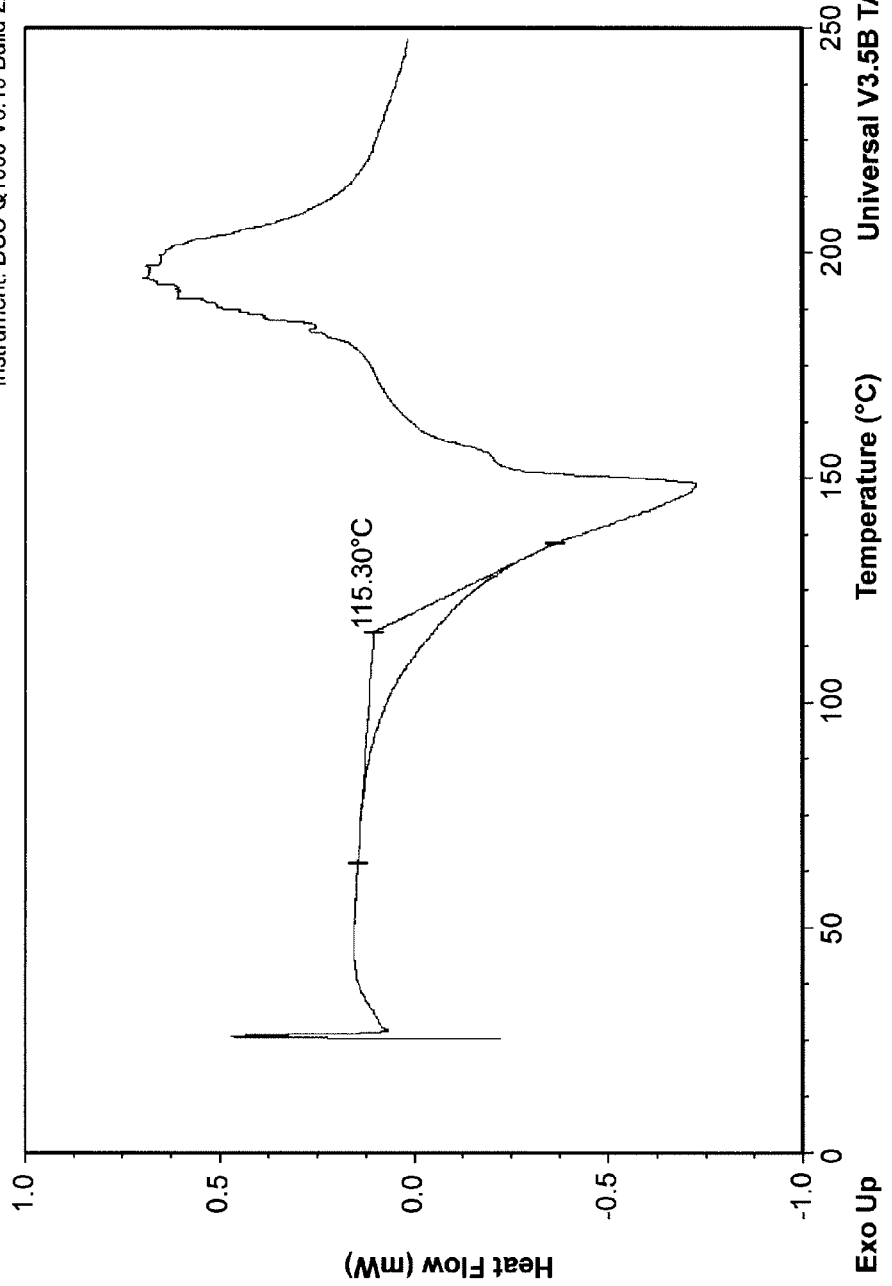
FIG. 4 shows the DSC curve of crystalline 1-(2-Fluoro-phenyl)-3-(2-oxo-5-phenyl-2,3-dihydro-1H-benzo[e][1,4]diazepin-3-yl)-urea besylate monohydrate.
Figure 5:
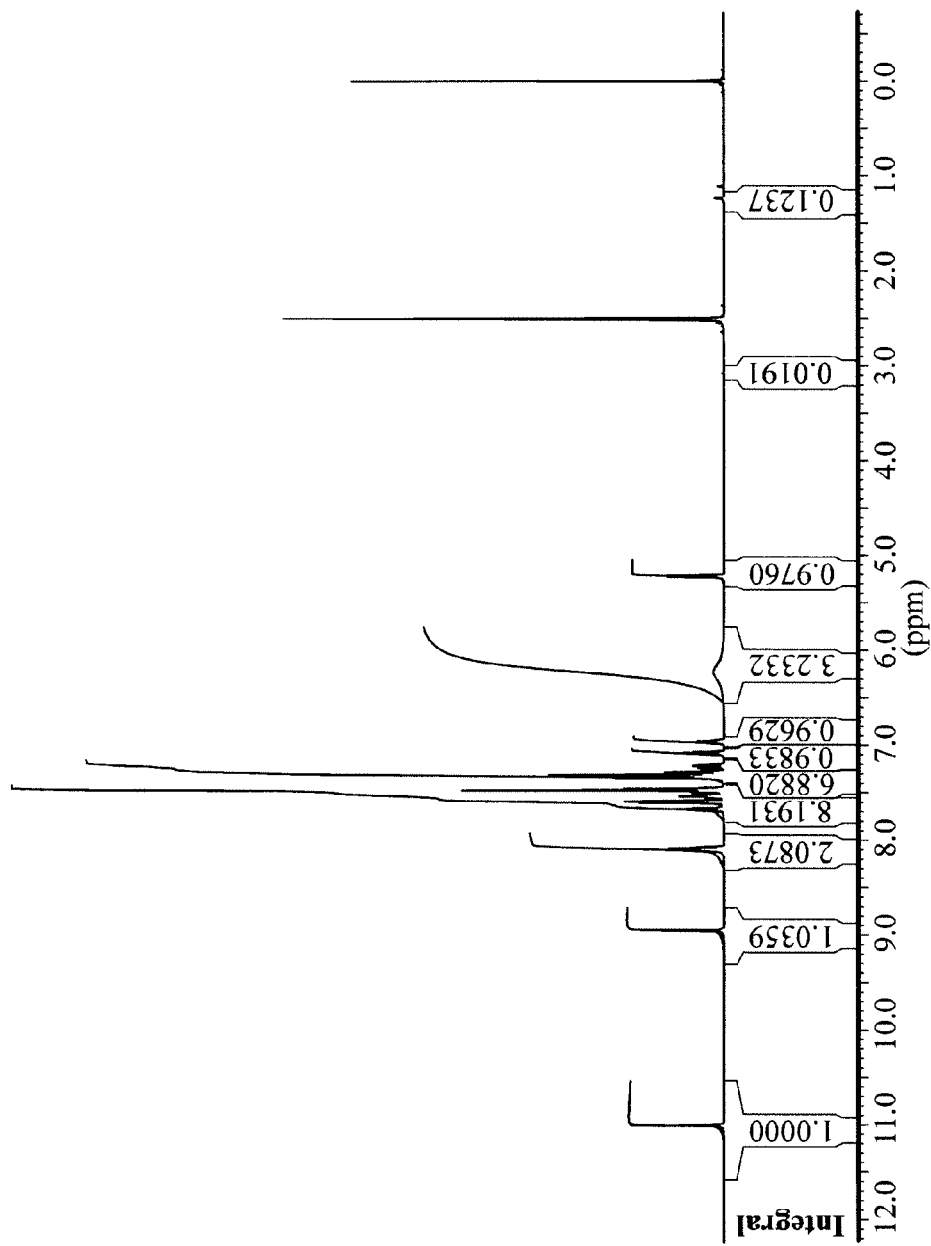
FIG. 5 shows NMR of crystalline 1-(2-Fluoro-phenyl)-3-(2-oxo-5-phenyl-2,3-dihydro-1H-benzo[e][1,4]diazepin-3-yl)-urea besylate monohydrate.

The invention also includes a process for the preparation of a besylate salt of the invention which comprises reacting the compound of formula I in free base form with an appropriate benzene sulfonic acid form and recovering from the reaction mixture the resultant salt. The process of the invention may be effected in conventional manner, e.g. by reaction in an appropriate inert solvent such as acetone, acetonitrile, ethyl acetate or t-butyl methyl ether.

In accordance with the present invention a process for the crystallization of 1-(2-Fluoro-phenyl)-3-(2-oxo-5-phenyl-2,3-dihydro-1H-benzo[e][1,4]diazepin-3-yl)-urea besylate is provided. The precise conditions under which crystals are formed may now be empirically determined and a number of methods are suitable in practice, including the crystallization conditions as described in Examples 1 to 3.

Crystallization-inducing conditions normally involve the use of an appropriate crystallization-inducing solvent, such as ethyl acetate or t-butyl methyl ether. Conveniently, the compound is dissolved in the solvent at ambient temperature. The solution may be produced by dissolving in a solvent any one or more forms of the compound, and solvates thereof, such as hydrate. Crystals may then be formed by conversion from free base to salt, crystallization taking place at a temperature of between about 0° C. as above and 40° C., preferably at ambient temperature. The dissolution and crystallization may be carried out in various conventional ways. For instance, free base may be dissolved in a solvent or a mixture of solvents in which it is readily soluble at ambient temperatures but in which besylate salt is only sparingly soluble at the same temperatures. Dissolution of the free base at elevated temperature followed by cooling after salt formation can also help the besylate salt crystals crystallize out of solution. Mixed solvents comprising a good solvent in which the compound is readily soluble, preferably, in amounts of at least 10% by weight at 20° C., and a poor solvent in which it is more sparingly soluble, preferably in amounts of not more than about 0.1% by weight at 20° C., may also be employed provided that crystallization from the mixture at a reduced temperature of normally at least about 0° C., is possible using the selected solvent mixture.

Alternatively, the difference in solubility of the crystals in different solvents may be used. For example, the free base may be dissolved in a good solvent in which it is highly soluble such as ethyl acetate or acetone in which it is soluble in amounts of at least 1% by weight at about 20° C. and the converted salt solution subsequently mixed with a poor solvent in which it is more sparingly soluble, such as one in which it is soluble in amounts of not more than about 0.1% by weight at about 20° C. Thus, the solution of the free base in the good solvent may be added to the benzenesulfonic acid in poor solvent, while maintaining normally a temperature in excess of about 20° C., or the poor solvent may be added to the solution of the converted besylate salt in the good solvent, again while normally maintaining a temperature in excess of about 20° C. Examples of good solvents for free base may include acetone or ethyl acetate. Examples of a poor solvents for the besylate salt may include ethyl acetate or t-butyl methyl ether or water. Preferably, crystallization is effected at a temperature in the range of about 0° C. to about 40° C.

In an alternative embodiment of the process of the invention, solid free base is suspended at a temperature of normally at least about 20° C. in a solvent in which it is incompletely soluble, preferably only sparingly soluble, at that temperature. A suspension results in which particles of solid are dispersed, and remain incompletely dissolved in the solvent. Preferably the solids are maintained in a state of suspension by agitation e.g. by shaking or stirring. The suspension is kept at a temperature of normally about 20° C. or higher in order to effect a conversion of the free base into besylate salt. The free base suspended in a suitable solvent may be amorphous or crystalline, it may also be a solvate, e.g. hydrate.

Conveniently, "seeds" of crystalline material can be added, if available, to the solution in order to induce crystallization.

In accordance with a preferred embodiment of the present invention, the crystalline forms of 1-(2-Fluoro-phenyl)-3-(2-oxo-5-phenyl-2,3-dihydro-1H-benzo[e][1,4]diazepin-3-yl)-urea besylate, e.g. the monohydrate thereof, have a high crystallinity. A crystal form is defined herein as having a "high crystallinity" or being "crystallographically pure" when it contains at most about 0.5% (w/w), e.g. at most about 0.1% (w/w) of other form. Thus e.g. "crystallographically pure Form A" contains about 0.5% (w/w) or less, e.g. about 0.1% (w/w) or less of another crystallographic form and/or amorphous form.

In one aspect the present invention provides pharmaceutical composition comprising an effective amount of a compound of the present invention. In a preferred embodiment, such a composition is a high dose formulation of 1-(2-Fluoro-phenyl)-3-(2-oxo-5-phenyl-2,3-dihydro-1H-benzo[e][1,4]diazepin-3-yl)-urea including e.g. at least 50 mg, preferably at least 100 mg, more preferably at least 250 mg 1-(2-Fluoro-phenyl)-3-(2-oxo-5-phenyl-2,3-dihydro-1H-benzo[e][1,4]diazepin-3-yl)-urea besylate and a suitable pharmaceutical carrier or diluent. In another preferred example, such a composition is an IV formulation, comprising e.g. 5 mg to 500 mg 1-(2-Fluoro-phenyl)-3-(2-oxo-5-phenyl-2,3-dihydro-1H-benzo[e][1,4]diazepin-3-yl)-urea besylate and a suitable pharmaceutical carrier or diluent.

One embodiment provides methods of preventing or treating infections of a warm-blooded animal, especially a human, by virus comprising administering an effective amount of a compound of the present invention. In a preferred embodiment the infection is viral infection disclosed in WO2004/026843, in particular a Respiratory Syncytial Virus (RSV) or for instance an influenza virus, a metapneumovirus, measles, parainfluenza or mumps virus. In a preferred embodiment the viruses infect mammals, more preferable humans.

The present invention further includes:
 a pharmaceutical composition comprising a salt or a crystalline salt of the invention together with at least one pharmaceutically acceptable carrier or diluent;

a pharmaceutical composition comprising a salt or a crystalline salt of the invention in combination with an anti-inflammatory compound as described in WO2004/026843;

a pharmaceutical composition comprising the compound of formula I in free form or pharmaceutically acceptable salt form other than a benzene sulfonic acid addition salt form, whenever prepared from a salt or a crystalline salt of the invention;

a salt or a crystalline salt of the invention for use as a pharmaceutical;

a salt or a crystalline salt of the invention for use in the preparation of a medicament;

a salt or a crystalline salt of the invention whenever prepared by a process as defined above;

a salt or a crystalline salt of formula I in free base form or salt form other than a benzene sulfonic acid addition salt form, whenever prepared from a salt or a crystalline salt of the invention;

the use of a compound of the invention in the preparation of a medicament for the treatment, e.g. orally or intravenously, of diseases susceptible of therapy with the salt or the crystalline salt of formula I in free base form or salt form, such as viral diseases;

a process for the preparation of a pharmaceutical composition which comprises mixing a salt or a crystalline salt of the invention together with at least one pharmaceutically acceptable carrier or diluent; and a method for the prophylactic or curative treatment of viral diseases such as RSV infection, comprising administration of a therapeutically effective amount of a salt or a crystalline salt of the invention to a subject in need of such treatment.

The crystalline forms of the present invention are synthesized in accordance with the following examples which are illustrative without limiting the scope of the present invention.

EXAMPLE 1

Preparation of RSV604 Besylate Monohydrate Salt

1). About 50 mg of RSV604 free base was dissolved in 2 ml of acetone (or acetonitrile).
2). About 40 mg of benzenesulfonic acid (hydrate, 97% pure) was added to the clear solution. Precipitation occurred after a few minutes. Keep stirring for 2 hours.
3). 2 to 4 ml of MtBE was added slowly as antisolvent.
4). Stir the slurry for 2 hours, then filter the solid
5). Dry the solid in vacuum oven at ambient temperature overnight.

EXAMPLE 2

Preparation of RSV604 Besylate Monohydrate Salt

1) Charge 2-L Argonaut reactor with 45 g of (S)-1-(2-fluorophenyl)-3-(2-oxo-5-phenyl-2,3-dihydro-1H-benzo[e][1,4]diazepin-3-yl)-urea (A9) and 1420.6 g of ethyl acetate.
2) Stir the reaction mixture at 20±3° C. for 10 min.
3) Add 188 g of DI water at 20±3° C. over 5 min resulting in a clear solution. Stir the solution for 20 min and separate the aqueous layer. Wash the organic layer twice with 188 g of DI water and separate the aqueous layer.
4) Add 250 mL (301 g) of saturated NaCl solution and separate the aqueous layer.
5) Charge another flask at 20±3° C. with 41.65 g of benzenesulfonic acid hydrate (containing 12% water) and 299.5 g of ethyl acetate. Stir at this temperature until the formation of a clear solution (20 min).
6) Slowly add A9 in ethyl acetate solution (above) to the benzenesulfonic acid solution (1 h 10 min). The solids form after adding about 70% by volume of A9 solution. Stir at 20±3° C. for 2 h after completion of addition.
7) Filter off the solids through a polypropylene filter cloth in a Büchner funnel (6 cm diameter), then wash the flask and filter cake (3 cm height) twice with a total amount of 170 g of ethyl aceate.
8) Dry the wet cake at 50±2° C. (20 mbar) for 16 h until EtOAc≦0.5% and Water≦5% to give 51 g of A11 as a off-white solid in 78% yield with 99% purity.

EXAMPLE 3

Preparation of RSV604 Anhydrous Besylate Salt

1) Charge a 250 mL flask with 3.0 g of benzenesulfonic acid hydrate (containing 12% water) and 160 mL of acetone. Stir at room temperature for 30 min and all solids dissolve.
2) Then add 4 g of (S)-1-(2-fluorophenyl)-3-(2-oxo-5-phenyl-2,3-dihydro-1H-benzo[e][1,4]diazepin-3-yl)-urea (A9). Stir at 20±3° C. for 30 min and all solids dissolve.
3) Add 190 mL of methyl tert-butyl ether at 20±3° C. over 20 min and stir the suspension for 16 h.
4) Filter off the solids through a polypropylene filter cloth in a Büchner funnel (6 cm diameter), then wash the flask and filter cake twice with a total amount of 60 mL of methyl tert-butyl ether
5) Dry the wet cake at 50±2° C. (20 mbar) for 16 h to give 5.4 g of the salt as yellow solids in 96% yield with 99% purity.

EXAMPLE 4

Elemental Analysis on Besylate Monohydrate

| Elemental analysis | Besylate monohydrate (TRD1312-34-30) | |
| --- | --- | --- |
|  | calcul. | found |
| % C | 59.57 | 59.27 |
| % H | 4.63 | 3.77 |
| % N | 9.92 | 9.86 |
| % F | 3.37 | 3.51 |
| % O | 17.00 | — |
| % S | 5.68 | 5.76 |

The invention claimed is:
1. A crystalline salt of 1-(2-Fluoro-phenyl)-3-(2-oxo-5-phenyl-2,3-dihydro-1H-benzo[e][1,4]diazepin-3-yl)-urea with benzenesulfonic acid in a crystalline form selected from the group consisting of besylate monohydrate and besylate anhydrate.
2. Crystalline 1-(2-Fluoro-phenyl)-3-(2-oxo-5-phenyl-2,3-dihydro-1H-benzo[e][1,4]diazepin-3-yl)-urea according to claim 1, wherein the crystalline form is besylate monohydrate.
3. Crystalline 1-(2-Fluoro-phenyl)-3-(2-oxo-5-phenyl-2,3-dihydro-1H-benzo[e][1,4]diazepin-3-yl)-urea according to claim 1, wherein the crystalline form is besylate anhydrate.

4. A crystalline salt according to claim 2 wherein said crystalline form has at least one X-ray pattern peak position at an angle of diffraction 2theta of 7.5°±0.5° or 21.3°±0.5° or 23.1°±0.5°.

5. A crystalline salt according to claim 3 which wherein said crystalline form has at least one X-ray pattern peak position at an angle of diffraction 2theta of 25.1°±0.5° or 14.5°±0.5° or 22.7°±0.5° or 22.1°±0.5° or 20.2°±0.5° or 23.7°±0.5°.

Figure 6:
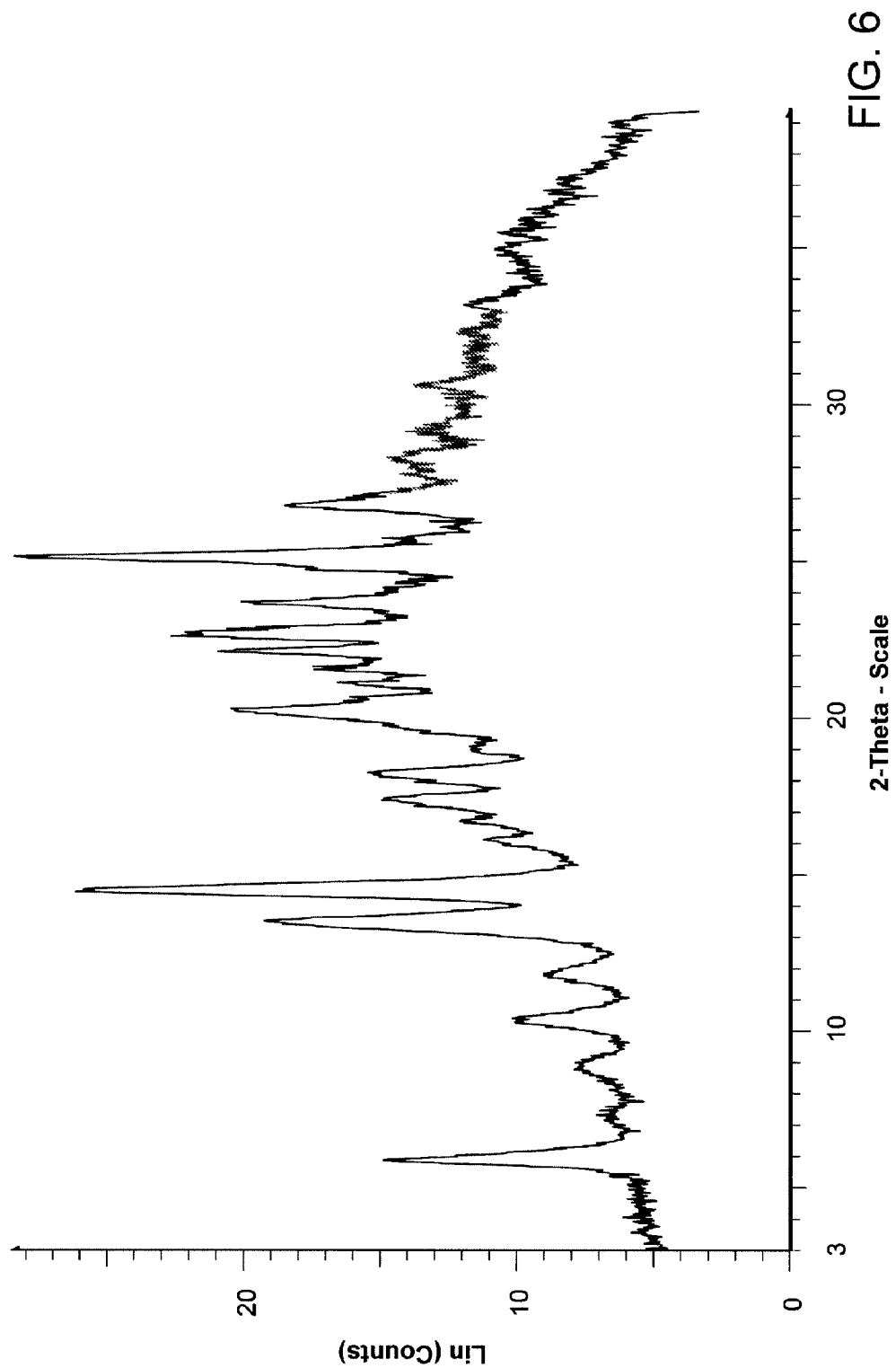

6. A crystalline salt according to claim 1 that exhibits an X-ray powder diffraction pattern as shown in FIG. 1 or FIG. 6.

7. A salt or a crystalline salt of 1-(2-Fluoro-phenyl)-3-(2-oxo-5-phenyl-2,3-dihydro-1H-benzo[e][1,4]diazepin-3-yl)-urea according to claim 1 which is present in essentially pure form.

8. A crystalline salt of 1-(2-Fluoro-phenyl)-3-(2-oxo-5-phenyl-2,3-dihydro-1H-benzo[e][1,4]diazepin-3-yl)-urea according to claim 1 having a high crystallinity.

9. A process for the preparation of a crystalline besylate salt of 1-(2-Fluoro-phenyl)-3-(2-oxo-5-phenyl-2,3-dihydro-1H-benzo[e][1,4]diazepin-3-yl)-urea according to claim 2 comprising appropriately converting the free base of 1-(2-Fluoro-phenyl)-3-(2-oxo-5-phenyl-2,3-dihydro-1H-benzo[e][1,4]diazepin-3-yl)-urea from a solution into crystalline besylate salt thereof under crystallization-inducing conditions.

10. A process for the preparation of a crystalline besylate salt of 1-(2-Fluoro-phenyl)-3-(2-oxo-5-phenyl-2,3-dihydro-1H-benzo[e][1,4]diazepin-3-yl)-urea according to claim 2 comprising the steps of dissolving 1-(2-Fluoro-phenyl)-3-(2-oxo-5-phenyl-2,3-dihydro-1H-benzo[e][1,4]diazepin-3-yl)-urea and benzene sulfonic acid in an appropriate solvent, optionally seeding the solution with besylate salt of 1-(2-Fluoro-phenyl)-3-(2-oxo-5-phenyl-2,3-dihydro-1H-benzo[e][1,4]diazepin-3-yl)-urea, and crystallizing the besylate salt in a poor solvent such as ethyl acetate or t-butyl methyl ether.

11. A process for the preparation of a crystalline besylate salt of 1-(2-Fluoro-phenyl)-3-(2-oxo-5-phenyl-2,3-dihydro-1H-benzo[e][1,4]diazepin-3-yl)-urea-one according to claim 2 comprising the step of crystallization or re-crystallization a besylate salt of 5 1-(2-Fluoro-phenyl)-3-(2-oxo-5-phenyl-2,3-dihydro-1H-benzo[e][1,4]diazepin-3-yl)-urea in a solution comprising acetone, acetonitrile, ethyl acetate or t-butyl methyl ether.

12. A pharmaceutical composition comprising a crystalline form of a besylate salt according to claim 1.

13. A high dose pharmaceutical composition comprising at least 50 mg of a crystalline form of a besylate salt according to claim 1 and a pharmaceutically acceptable carrier or diluent.

14. A pharmaceutical composition for intravenous application comprising a crystalline form of a besylate salt according to claim 1 and a pharmaceutically acceptable carrier or diluent.

15. A method of treating an RSV infection, comprising administering to a patient in need a therapeutically effective amount of a crystalline form of a besylate salt according to claim 1.

* * * * *